United States Patent
Lee et al.

(10) Patent No.: US 10,905,382 B2
(45) Date of Patent: Feb. 2, 2021

(54) BIO-SIGNAL QUALITY ASSESSMENT APPARATUS AND METHOD AND BIO-SIGNAL MEASUREMENT PARAMETER OPTIMIZATION APPARATUS AND METHOD

(71) Applicant: SAMSUNG ELECTRONICS CO., LTD., Suwon-si (KR)

(72) Inventors: Jong Wook Lee, Suwon-si (KR); Byung Hoon Ko, Hwaseong-si (KR); Jin Hyun Yun, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 705 days.

(21) Appl. No.: 15/459,128

(22) Filed: Mar. 15, 2017

(65) Prior Publication Data

US 2018/0110470 A1 Apr. 26, 2018

(30) Foreign Application Priority Data

Oct. 25, 2016 (KR) ........................ 10-2016-0139407

(51) Int. Cl.
*A61B 5/00* (2006.01)
*A61B 5/024* (2006.01)

(52) U.S. Cl.
CPC .......... *A61B 5/7221* (2013.01); *A61B 5/0015* (2013.01); *A61B 5/02416* (2013.01); *A61B 5/7235* (2013.01); *A61B 5/742* (2013.01)

(58) Field of Classification Search
CPC . A61B 5/7221; A61B 5/02416; A61B 5/7225; A61B 5/02007; A61B 5/00; G06K 9/0053
See application file for complete search history.

(56) References Cited

U.S. PATENT DOCUMENTS

| | | | |
|---|---|---|---|
| 5,329,554 A | 7/1994 | Behrens et al. | |
| 7,052,465 B1 | 5/2006 | Lunak et al. | |
| 7,254,425 B2 * | 8/2007 | Lowery | A61B 5/14532 600/310 |
| 8,100,835 B2 | 1/2012 | Baruch | |

(Continued)

FOREIGN PATENT DOCUMENTS

| | | |
|---|---|---|
| JP | 3196871 B2 | 8/2001 |
| JP | 2009297367 A | 12/2009 |

(Continued)

OTHER PUBLICATIONS

"The Mobile Healthcare (mHealth) Bible: 2014-2020", SNS Research, Reportlinker, Sep. 2013 (17 pages total).

(Continued)

*Primary Examiner* — Keith M Raymond
*Assistant Examiner* — Patrick M Mehl
(74) *Attorney, Agent, or Firm* — Sughrue Mion, PLLC

(57) ABSTRACT

A bio-signal quality assessment apparatus, a bio-signal quality assessment method, a bio-signal measurement parameter optimization apparatus, and bio-signal measurement parameter optimization apparatus method are provided. The bio-signal quality assessment apparatus includes a processor configured to determine a moving average of a bio-signal, and assess a quality of the bio-signal, based on a comparison between the determined moving average and the bio-signal.

21 Claims, 17 Drawing Sheets

(56) References Cited

U.S. PATENT DOCUMENTS

| | | |
|---|---|---|
| 8,731,254 B2 | 5/2014 | Nakao et al. |
| 8,768,438 B2 | 7/2014 | Mestha et al. |
| 8,929,963 B2 | 1/2015 | Lisogurski |
| 9,044,180 B2 | 6/2015 | LeBoeuf et al. |
| 2006/0178591 A1 | 8/2006 | Hempfling |
| 2009/0326395 A1 | 12/2009 | Watson |
| 2011/0077531 A1* | 3/2011 | Watson .................. A61B 5/021 600/485 |
| 2011/0196247 A1* | 8/2011 | Cao ....................... A61B 5/0464 600/509 |
| 2012/0065525 A1 | 3/2012 | Douniama et al. |
| 2012/0095304 A1* | 4/2012 | Biondi ................... G16H 50/20 600/301 |
| 2013/0324812 A1 | 12/2013 | Brainard, II et al. |
| 2014/0073975 A1* | 3/2014 | Engelbrecht ......... A61B 5/7203 600/502 |
| 2015/0112606 A1 | 4/2015 | He et al. |
| 2015/0148691 A1 | 5/2015 | Moyer et al. |
| 2015/0220486 A1 | 8/2015 | Karakonstantis et al. |
| 2016/0120482 A1 | 5/2016 | Kirenko et al. |

FOREIGN PATENT DOCUMENTS

| | | | |
|---|---|---|---|
| KR | 20100033875 | * 3/2010 | .............. A61B 5/02 |
| KR | 101019764 B1 | 3/2011 | |
| WO | 2013/009423 A1 | 1/2013 | |

OTHER PUBLICATIONS

Communication issued by the European Patent Office dated Nov. 24, 2017 in counterpart European Patent Application No. 17172685.4.

* cited by examiner

BIO-SIGNAL QUALITY ASSESSMENT APPARATUS AND METHOD AND BIO-SIGNAL MEASUREMENT PARAMETER OPTIMIZATION APPARATUS AND METHOD

CROSS-REFERENCE TO RELATED APPLICATION

This application claims priority from Korean Patent Application No. 10-2016-0139407, filed on Oct. 25, 2016, in the Korean Intellectual Property Office, the disclosure of which is incorporated herein by reference in its entirety.

BACKGROUND

1. Field

Apparatuses and methods consistent with example embodiments relate to a bio-signal quality assessment apparatus, a bio-signal quality assessment method, a bio-signal measurement parameter optimization apparatus, and bio-signal measurement parameter optimization apparatus method.

2. Description of Related Art

Healthcare technologies have attracted much attention due to the rapid entry into an aging society and relevant social problems such as increases in medical expenses. Accordingly, not only medical devices that can be utilized in hospitals and inspection agencies but also small-sized medical devices that can be carried by individuals such as wearable devices, are being developed.

A user's heart rate, stress and blood pressure may be measured based on the user's bio-signal, and bio-signals of good quality are collected to increase the accuracy of the measurement result.

Signal quality may be assessed by a signal-to-noise ratio (SNR) that refers to the intensity of a signal relative to a noise, and complex calculations, such as Fourier transform and post-processing, may be performed to compute the SNR.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, there is provided a bio-signal quality assessment apparatus including a processor configured to determine a moving average of a bio-signal, and assess a quality of the bio-signal, based on a comparison between the determined moving average and the bio-signal.

The bio-signal may be a photoplethysmography signal.

The moving average may be an exponentially weighted moving average.

The processor may be further configured to divide the bio-signal into sections, compare the determined moving average to each value of bio-signal samples of the bio-signal to determine whether each of the bio-signal samples satisfies a predetermined condition, determine a number of the bio-signal samples satisfying the predetermined condition, in each of the sections, based on a result of the determination of whether each of the bio-signal samples satisfies the predetermined condition, and assess the quality of the bio-signal, based on the determined number of the bio-signal samples in each of the sections.

The processor may be further configured to determine, in each of the sections, the number of the bio-signal samples having values greater than the determined moving average or the number of the bio-signal samples having values less than the determined moving average.

The processor may be further configured to determine a variance or a standard deviation of the determined number of the bio-signal samples in each of the sections, and assess the quality of the bio-signal, using the determined variance or the determined standard deviation as a bio-signal quality index.

The processor may be further configured to assess that the quality of the bio-signal is better as the determined variance or the determined standard deviation is larger.

The bio-signal quality assessment apparatus may further include a bio-signal measurer configured to measure the bio-signal.

The bio-signal measurer may include a light source configured to emit light onto a subject, and a photodetector configured to measure the bio-signal by detecting light that is reflected or scattered from the subject.

The bio-signal quality assessment apparatus may further include a data receiver configured to receive data of the bio-signal from an external device.

According to an aspect of an example embodiment, there is provided a bio-signal quality assessment method including determining a moving average of a bio-signal, and assessing a quality of the bio-signal, based on a comparison between the determined moving average and the bio-signal.

The bio-signal may be a photoplethysmography signal.

The moving average may be an exponentially weighted moving average.

The bio-signal quality assessment method may further include dividing the bio-signal into sections, comparing the determined moving average to each value of bio-signal samples of the bio-signal to determine whether each of the bio-signal samples satisfies a predetermined condition, determining a number of the bio-signal samples satisfying the predetermined condition, in each of the sections, based on a result of the determination of whether each of the bio-signal samples satisfies the predetermined condition, and assessing the quality of the bio-signal, based on the determined number of the bio-signal samples in each of the sections.

The determining of the number of the bio-signal samples in each of the sections may include determining, in each of the sections, the number of the bio-signal samples having values greater than the determined moving average or the number of the bio-signal samples having values less than the determined moving average.

The bio-signal quality assessment method may further include determining a variance or a standard deviation of the determined number of the bio-signal samples in each of the sections, and the assessing of the quality of the bio-signal may include assessing the quality of the bio-signal, using the determined variance or the determined standard deviation as a bio-signal quality index.

The assessing of the quality of the bio-signal may further include assessing that the quality of the bio-signal is better as the determined variance or the determined standard deviation is larger.

The bio-signal quality assessment method may further include measuring the bio-signal.

The bio-signal quality assessment method may further include emitting light onto a subject, and the measuring of the bio-signal may include measuring the bio-signal by detecting light that is reflected or scattered from the subject.

The bio-signal quality assessment method may further include receiving data of the bio-signal from an external device.

According to an aspect of an example embodiment, there is provided a bio-signal measurement parameter optimization apparatus including a bio-signal measurer configured to emit light onto a subject, and measure a bio-signal by detecting light that is reflected or scattered from the subject. The bio-signal measurement parameter optimization apparatus further includes a processor configured to determine a bio-signal quality index, based on a comparison between the measured bio-signal and a moving average of the measured bio-signal, and adjust a bio-signal measurement parameter, based on the determined bio-signal quality index.

The bio-signal measurement parameter may include any one or any combination of an amount of the emitted light, an amplification gain, and a cancellation current.

The processor may be further configured to determine the moving average of the measured bio-signal, divide the measured bio-signal into sections, compare the determined moving average to each value of bio-signal samples of the measured bio-signal to determine whether each of the bio-signal samples satisfies a predetermined condition, determine a number of the bio-signal samples satisfying the predetermined condition, in each of the sections, based on a result of the determination of whether each of the bio-signal samples satisfies the predetermined condition, and determine a variance or a standard deviation of the determined number of the bio-signal samples in each of the sections, as the bio-signal quality index.

The processor may be further configured to determine, in each of the sections, the number of the bio-signal samples having values greater than the determined moving average or the number of the bio-signal samples having values less than the determined moving average.

The bio-signal may be a photoplethysmography signal.

The moving average may be an exponentially weighted moving average.

The processor may be further configured to adjust the bio-signal measurement parameter in response to the determined bio-signal quality index being less than or equal to a threshold value.

The processor may be further configured to measure bio-signals, a number of the measured bio-signals being predetermined, determine bio-signal quality indices of the measured bio-signals, and adjust the bio-signal measurement parameter in response to an average of the bio-signal quality indices being less than or equal to a threshold value.

According to an aspect of an example embodiment, there is provided a bio-signal measurement parameter optimization method including emitting light onto a subject, measuring a bio-signal by detecting light that is reflected or scattered from the subject, determining a bio-signal quality index, based on a comparison between the measured bio-signal and a moving average of the measured bio-signal, and adjusting a bio-signal measurement parameter, based on the determined bio-signal quality index.

The bio-signal measurement parameter may include any one or any combination of an amount of the emitted light, an amplification gain, and a cancellation current.

The bio-signal measurement parameter optimization method may further include determining the moving average of the measured bio-signal, dividing the measured bio-signal into sections, comparing the determined moving average to each value of bio-signal samples of the measured bio-signal to determine whether each of the bio-signal samples satisfies a predetermined condition, determining a number of the bio-signal samples satisfying the predetermined condition, in each of the sections, based on a result of the determination of whether each of the bio-signal samples satisfies the predetermined condition, and determining a variance or a standard deviation of the determined number of bio-signal samples in each of the sections, as the bio-signal quality index.

The determining of the number of the bio-signal samples in each of the sections may include determining, in each of the sections, the number of the bio-signal samples having values greater than the determined moving average or the number of the bio-signal samples having values less than the determined moving average.

The adjusting of the bio-signal measurement parameter may include adjusting the bio-signal measurement parameter in response to the determined bio-signal quality index being less than or equal to a threshold value.

According to an aspect of an example embodiment, there is provided an apparatus including a processor configured to determine a moving average of a bio-signal, and determine, in each of sections of the bio-signal, a number of bio-signal samples of the bio-signal having values greater than the determined moving average or a number of the bio-signal samples having values less than the determined moving average. The processor is further configured to determine a variance or a standard deviation of the determined number of the bio-signal samples having the values greater than the determined moving average or the number of the bio-signal samples having the values less than the determined moving average, in each of the sections, and assess that a quality of the bio-signal is better as the determined variance or the determined standard deviation is larger.

The processor may be further configured to adjust a parameter for measuring the bio-signal in response to the determined variance or the determined standard deviation being less than or equal to a threshold value.

BRIEF DESCRIPTION OF THE DRAWINGS

The above and/or other aspects will be more apparent by describing example embodiments with reference to the accompanying drawings, in which.

Figure 1:
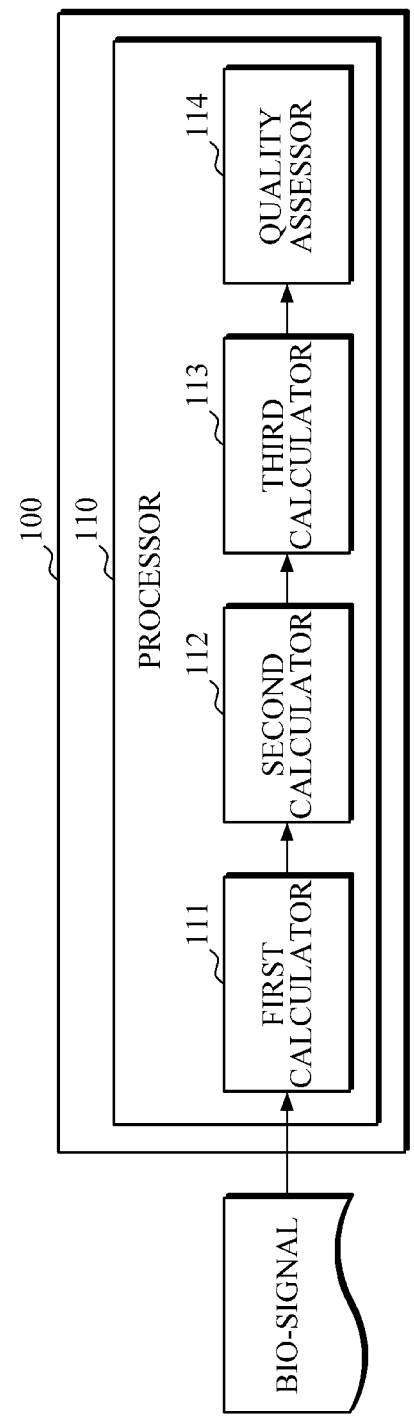
FIG. 1 is a block diagram illustrating a bio-signal quality assessment apparatus according to an example embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

In some alternative implementations, the functions/acts noted in the blocks may occur out of the order noted in the flowcharts. For example, two blocks shown in succession may in fact be executed substantially concurrently, or the blocks may sometimes be executed in the reverse order, depending upon the functionality/acts involved.

Terms described in below are selected by considering functions in example embodiments, and meanings may vary depending on, for example, a user or operator's intentions or customs. Therefore, in the example embodiments, when terms are defined, the meanings of terms may be interpreted based on definitions, and otherwise, may be interpreted based on meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element, or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a block diagram illustrating a bio-signal quality assessment apparatus 100 according to an example embodiment. The bio-signal quality assessment apparatus 100 may be an apparatus that may assess in real-time a quality of a bio-signal measured from a user through an efficient calculation. The bio-signal quality assessment apparatus 100 may be implemented in the form of a software module or fabricated in the form of a hardware chip and mounted in an electronic device. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, etc., and the wearable device may include a wristwatch type, a wrist band type, a ring type, a belt type, a necklace type, an ankle band type, a thigh band type, a forearm band type, and the like. However, the electronic device is not limited to the above-described examples, and the wearable device is also not limited to the above-described examples.

Referring to FIG. 1, the bio-signal quality assessment apparatus 100 includes a processor 110 that accesses the quality of a bio-signal on the basis of a moving average of the bio-signal. The processor 110 includes a first calculator 111, a second calculator 112, a third calculator 113, and a quality assessor 114.

The first calculator 111 may calculate a moving average of the bio-signal. In this case, the bio-signal may include a predetermined number of samples (hereinafter, referred to as "bio-signal samples"), and the number of bio-signal samples included in the bio-signal may be set in advance in consideration of a periodicity of the bio-signal as a basic unit of a bio-signal quality index calculation or a bio-signal quality assessment.

According to an example embodiment, the bio-signal may be a photoplethysmography (PPG) signal, and the moving average may be an exponentially weighted moving average. However, this is an example embodiment, and the present disclosure is not limited thereto.

According to an example embodiment, the first calculator 111 may calculate the moving average of the bio-signal, using Equation 1.

$$m[t]=m[t-1]*\alpha+s[t]*(1-\alpha) \quad (1)$$

Here, t denotes time, m[t] denotes a moving average at time t, s[t] denotes a value of a bio-signal sample measured at time t, and α denotes a weight. α may be set to various values depending on a performance and a use of the system, and whether to put more weight on an immediately preceding moving average, and a new bio-signal sample may be determined by adjusting α.

The second calculator 112 may divide the bio-signal into a plurality of sections. According to an example embodiment, the second calculator 112 may divide the bio-signal into the plurality of sections to include a predetermined number of bio-signal samples in each section. For example, under the assumption that a bio-signal includes one hundred bio-signal samples, the second calculator 112 may divide the bio-signal into five sections, each of which includes twenty bio-signal samples. In this case, the number of bio-signal samples included in each section may be set variously according to the performance or use of the system.

The second calculator 112 may compare the calculated moving average and the bio-signal, determine whether this comparison satisfies a predetermined condition, and calculate a number of bio-signal samples in each section that satisfy the predetermined condition. In this case, the predetermined condition may include that a magnitude of a sample value is greater than the moving average or that the magnitude of the sample value is less than the moving average. For example, the second calculator 112 may calculate the number of bio-signal samples in each section that have sample values greater than the moving average, or the number of bio-signal samples in each section that have sample values less than the moving average.

The third calculator 113 may calculate a variance or a standard deviation of the calculated number of bio-signal samples in each section that satisfy the predetermined condition.

The quality assessor 114 may asses the quality of the bio-signal, using the calculated variance or standard deviation as a bio-signal quality index. According to an example embodiment, the quality assessor 114 may assess the quality of the bio-signal, using a criterion predefined in consideration of a relationship between the bio-signal quality index and a signal-to-noise ratio (SNR). For example, the quality assessor 114 may categorize the quality of the bio-signal as "high," "moderate," or "low." The quality assessor 114 may assess the quality of the bio-signal as high when the variance or standard deviation calculated by the third calculator 113 is greater than or equal to a first threshold value, assess the quality as moderate when the calculated variance or standard deviation is less than the first threshold value and greater than or equal to a second threshold value, and assess the quality as low when the calculated variance or standard deviation is less than the second threshold value. In this case, the first threshold value and the second threshold value may be set in advance in consideration of the relationship between the SNR and the bio-signal quality index.

That is, the quality assessor 114 may assess that the quality of the bio-signal is better as the calculated variance or standard deviation is larger.

Figure 2:
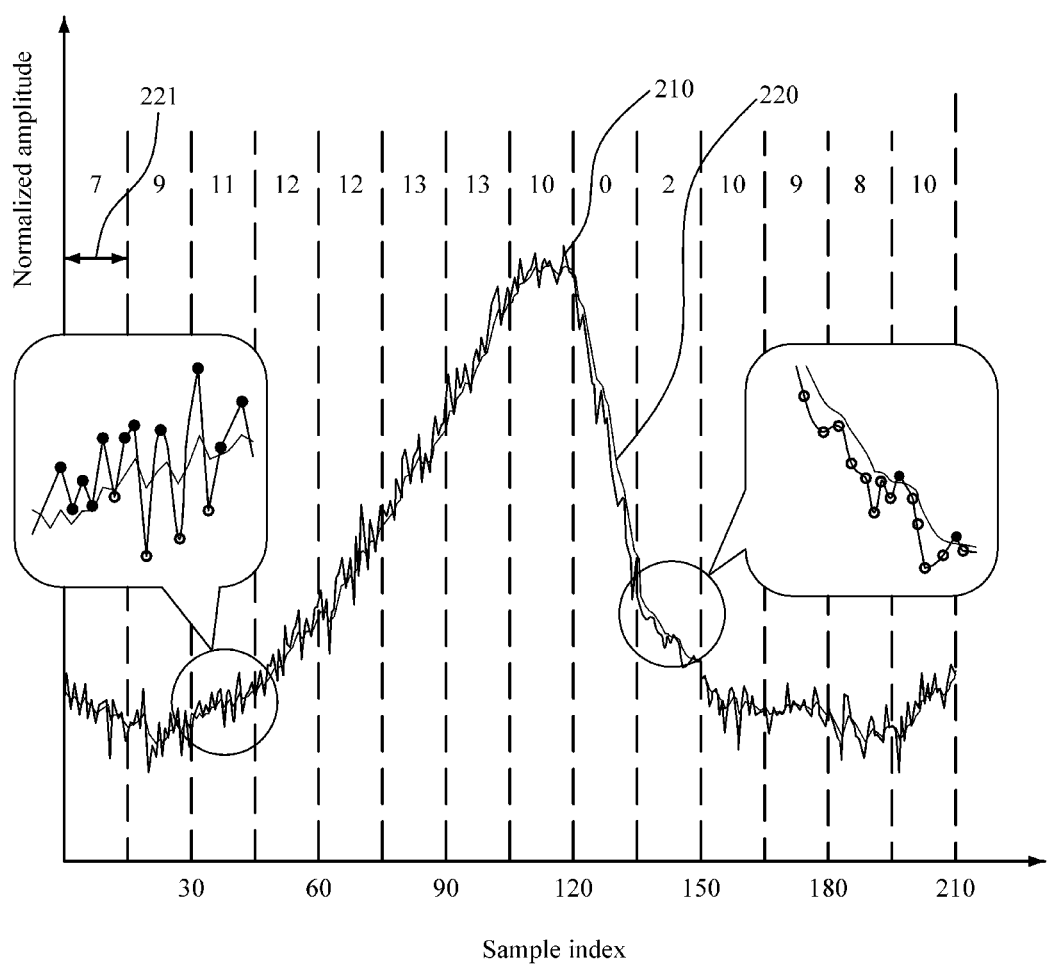
FIG. 2 is a graph for describing a method of calculating a bio-signal quality index, according to an example embodiment.

FIG. 2 is a graph for describing a method of calculating a bio-signal quality index, according to an example embodiment. In FIG. 2, a horizontal axis of the graph represents a sample index, and a vertical axis thereof represents a normalized sample value or amplitude. A bio-signal 210 includes two hundred and ten bio-signal samples, and the two hundred and ten bio-signal samples may be a basic unit of the bio-signal quality index calculation or a bio-signal quality assessment.

Referring to FIGS. 1 and 2, the first calculator 111 calculates a moving average 220 of the bio-signal 210. For example, the first calculator 111 may calculate the moving average 220, using Equation 1.

The second calculator 112 divides the bio-signal 210 into fourteen sections 221 so that each section includes fifteen bio-signal samples according to settings, and calculates a number of bio-signal samples in each section that have values greater than the moving average 220. In the illustrated example, there are seven bio-signal samples in the first section, nine bio-signal samples in the second section, eleven bio-signal samples in the third section, twelve bio-signal samples in the fourth section, twelve bio-signal samples in the fifth section, thirteen bio-signal samples in the sixth section, thirteen bio-signal samples in the seventh section, ten bio-signal samples in the eighth section, none in ninth section, two bio-signal samples in the tenth section, ten bio-signal samples in the eleventh section, nine bio-signal samples in the twelfth section, eight bio-signal samples in the thirteenth section, and ten bio-signal samples in the fourteenth section.

The third calculator 113 may calculate a variance with respect to the calculated number of bio-signal samples in each section that have values greater than the moving average 220. In the illustrated example, the third calculator 113 may obtain 14.77 as the variance of the calculated number of bio-signal samples in each section that have values greater than the moving average 220, and the calculated number of each section is 7 (the first section), 9 (the second section), 11 (the third section), 12 (the fourth section), 12 (the fifth section), 13 (the sixth section), 13 (the seventh section), 10 (the eighth section), 0 (the ninth section), 2 (the tenth section), 10 (the eleventh section), 9 (the twelfth section), 8 (the thirteenth section), and 10 (the fourteenth section).

The quality assessor 114 may assess the quality of the bio-signal 210 using the variance value 14.77 calculated by the third calculator 113 as the bio-signal quality index. At this time, the quality assessor 114 may assess the quality of the bio-signal 210 using a criterion predefined in consideration of the relationship between the bio-signal quality index (variance value 14.77) and the SNR.

Figure 3:
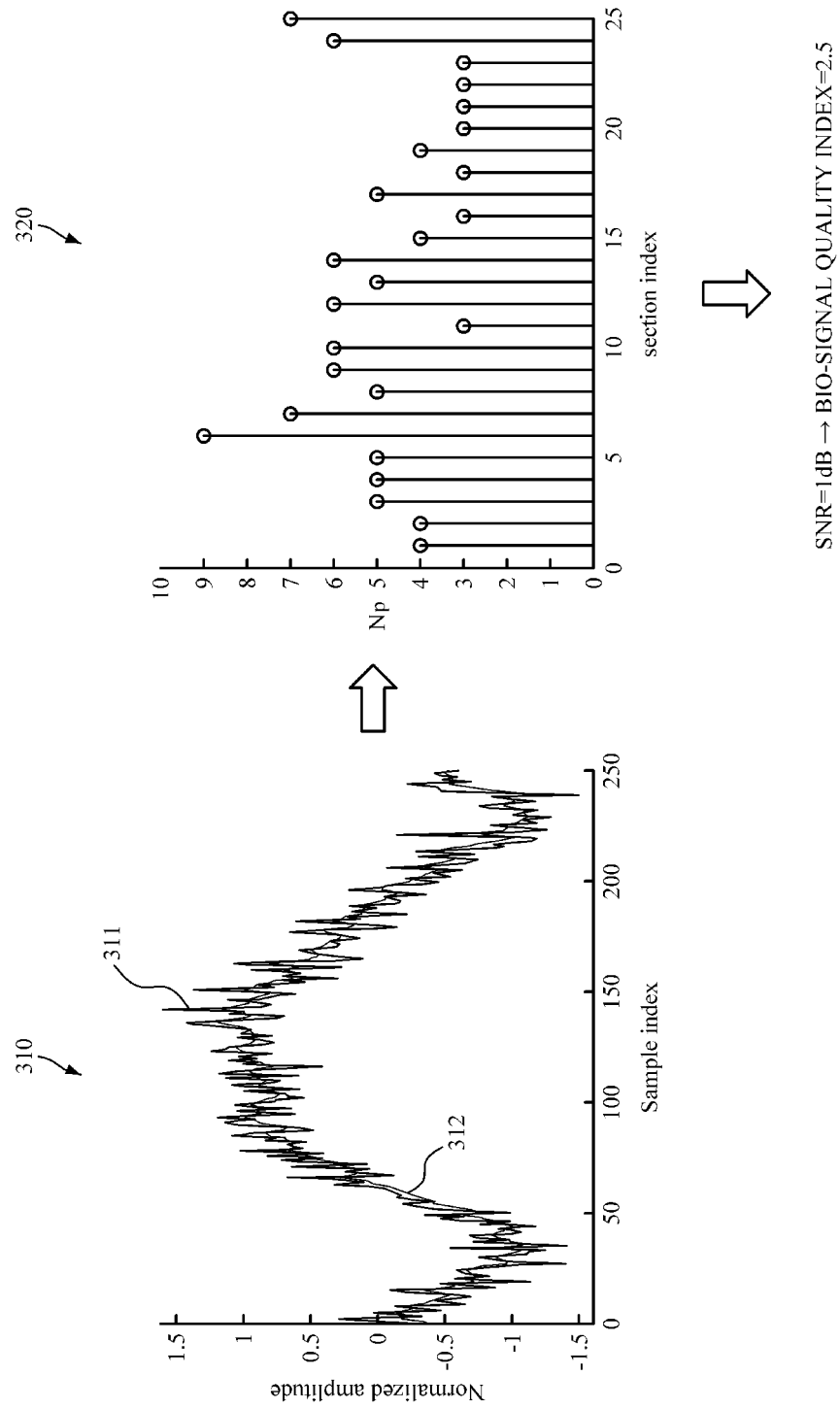
FIG. 3 is a diagram illustrating a bio-signal quality index calculated with respect to a low-quality bio-signal, according to an example embodiment.
Figure 4:
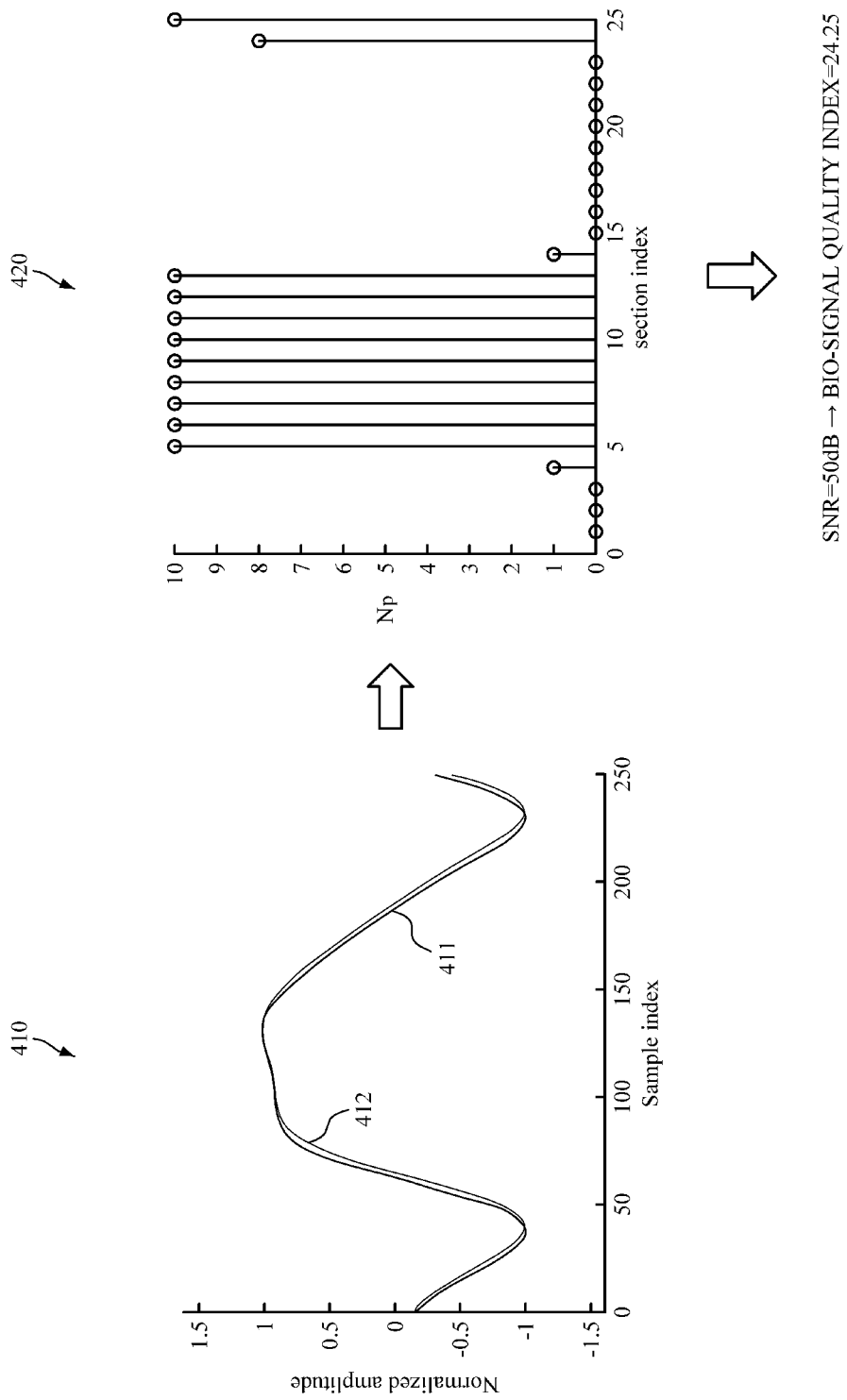
FIG. 4 is a diagram illustrating a bio-signal quality index calculated with respect to a high-quality bio-signal, according to an example embodiment.

FIGS. 3 and 4 are graphs for describing a relationship between an SNR and a bio-signal quality index, according to example embodiments. FIG. 3 is a diagram illustrating a bio-signal quality index calculated with respect to a low-quality bio-signal, according to an example embodiment, and FIG. 4 is a diagram illustrating a bio-signal quality index calculated with respect to a high-quality bio-signal, according to an example embodiment.

FIGS. 3 and 4 illustrate a case in which a bio-signal includes two hundred and fifty bio-signal samples, and each section includes ten bio-signal samples. That is, the bio-signal is divided into twenty five sections, each of which includes ten bio-signal samples.

Referring to FIG. 3, a graph 310 shows a bio-signal 311 having a SNR of 1 dB and a moving average 312 calculated from the bio-signal 311. A graph 320 shows a result of calculating a number Np of bio-signal samples in each section of the bio-signal 311 that have values greater than the moving average 312.

In the graph 320, the number of bio-signal samples in each section (a first section to a twenty-fifth section) that have values greater than the moving average 312 is 4, 4, 5, 5, 5, 9, 7, 5, 6, 6, 3, 6, 5, 6, 4, 3, 5, 3, 4, 3, 3, 3, 3, 6, and 7. A variance with respect to the calculated number (4, 4, 5, 5, 5, 9, 7, 5, 6, 6, 3, 6, 5, 6, 4, 3, 5, 3, 4, 3, 3, 3, 3, 6, and 7) of bio-signal samples having values greater than the moving average 312 in each section is calculated as 2.5.

That is, the bio-signal quality index of the bio-signal 311 having an SNR of 1 dB is 2.5.

Referring to FIG. 4, a graph 410 shows a bio-signal 411 having an SNR of 50 dB and a moving average 412 calculated from the bio-signal 411. A graph 420 shows a result of calculating a number Np of bio-signal samples in each section of the bio-signal 411 that have values greater than the moving average 412.

In the graph 420, the number of bio-signal samples in each section (a first section to a twenty-fifth section) that have values greater than the moving average 412 is 0, 0, 0, 1, 10, 10, 10, 10, 10, 10, 10, 10, 10, 1, 0, 0, 0, 0, 0, 0, 0, 0, 0, 8, and 10. A variance with respect to the calculated number (0, 0, 0, 1, 10, 10, 10, 10, 10, 10, 10, 10, 10, 1, 0, 0, 0, 0, 0, 0, 0, 0, 0, 8, and 10) of bio-signal samples having values greater than the moving average 312 in each section is calculated as 24.25.

That is, the bio-signal quality index of the bio-signal 411 having an SNR of 50 dB is 24.25.

Referring to FIGS. 3 and 4, it is seen that the SNR and the bio-signal quality index have a positive correlation. In other words, it is seen that the larger the biological signal quality index is, the greater the SNR of the biological signal is, that is, the better a quality of the biological signal is.

Figure 5:
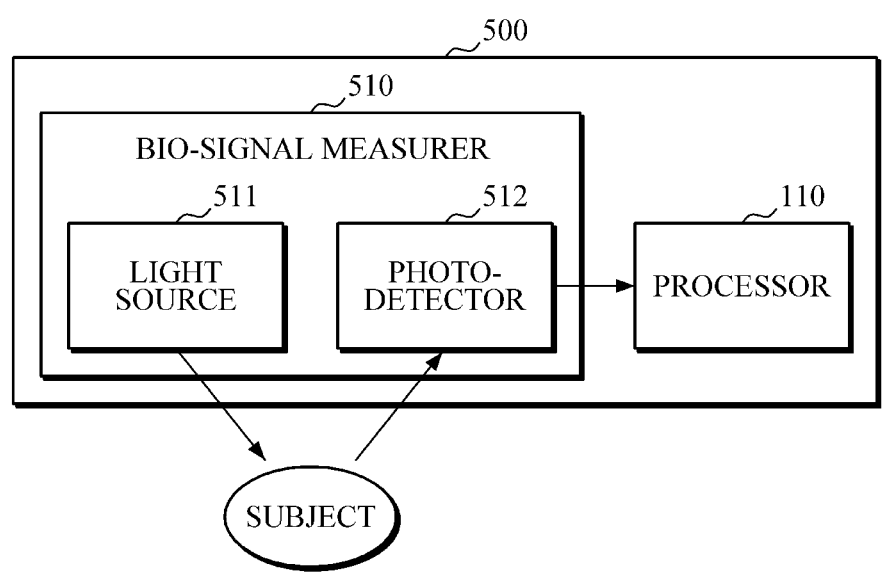
FIG. 5 is a block diagram illustrating a bio-signal quality assessment apparatus according to another example embodiment.

FIG. 5 is a block diagram illustrating a bio-signal quality assessment apparatus 500 according to another example embodiment.

Referring to FIG. 5, the bio-signal quality assessment apparatus 500 includes a bio-signal measurer 510 and a processor 110. Because the processor 110 is the same as described above with reference to FIG. 1, a detailed description thereof will be omitted.

The bio-signal measurer 510 may measure a bio-signal with respect to a subject. To this end, the bio-signal measurer 510 includes a light source 511 and a photodetector 512.

The light source 511 may emit light onto the subject. According to an example embodiment, the light source 511 may include various light emitting devices, such as a light emitting diode (LED), a laser diode, and the like.

The photodetector 510 may detect light reflected or scattered from the subject and generate an electrical signal corresponding to a bio-signal. According to an example embodiment, the photodetector 510 may include various light receiving elements, such as a photo diode, a photo transistor (PTr), a charge-coupled device (CCD), and the like.

The subject may be a living body part, as an object of a bio-signal measurement, which may be in contact with or in proximity to the bio-signal measurer 510, and may be a part of a human body where it is convenient to measure the bio-signal. For example, the subject may be an area of a wrist surface close to a radial artery. However, the subject is not limited to the above example, and may be a distal region of the human body, such as a finger, a toe, or the like, which is a region having a high density of blood vessels.

Figure 6:
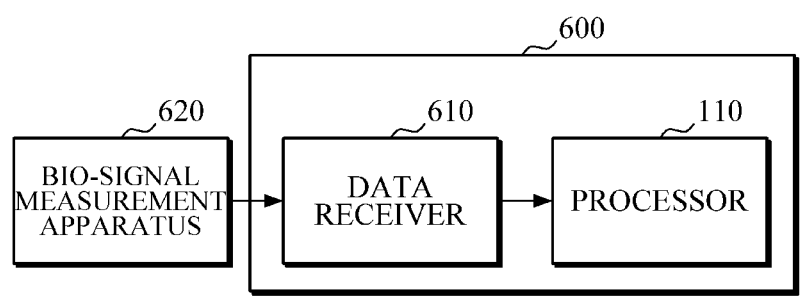
FIG. 6 is a block diagram illustrating a bio-signal quality assessment apparatus according to still another example embodiment.

FIG. 6 is a block diagram illustrating a bio-signal quality assessment apparatus 600 according to still another example embodiment.

Referring to FIG. 6, the bio-signal quality assessment apparatus 600 includes a data receiver 610 and a processor 110. Here, the processor 110 is the same as described above with reference to FIG. 1, and thus the detailed description thereof will be omitted.

The data receiver 610 may receive bio-signal data from a bio-signal measurement apparatus 620, using a communication technology. In this case, the communication technology may include, but not limited to, a Bluetooth communication, Bluetooth low energy (BLE) communication, a near-field communication (NFC), a wireless local area network (WLAN) communication, a ZigBee communication, an infrared data association (IrDA) communication, a Wi-Fi direct (WFD) communication, a ultra-wideband (UWB) communication, an Ant+ communication, a Wi-Fi communication, a radio frequency identification (RFID) communication, a 3G communication, a 4G communication, a 5G communication, and the like.

The bio-signal measurement apparatus 620 may measure a bio-signal of a subject in response to a control signal. For example, in response to a control signal generated according to an input of a user or a control signal received from the bio-signal quality assessment apparatus 600, the bio-signal measurement apparatus 620 may measure the bio-signal by driving a light source to emit light onto the subject and receiving light reflected or scattered from the subject.

A communication interface for wired/wireless communications may be mounted in the bio-signal measurement apparatus 620, and the bio-signal measurement apparatus 620 may transmit bio-signal data to the bio-signal quality assessment apparatus 600 through the communication interface.

The bio-signal measurement apparatus 620 may be a wearable device that may be worn on a user's body, but this is an example embodiment, and the bio-signal measurement apparatus 620 is not limited thereto. That is, a type of the bio-signal measurement apparatus 620 may not be particularly limited in terms of a size or a portability of the apparatus. For example, the bio-signal measurement apparatus 620 may be an apparatus that is installed as a fixed type in a medical institution and measures bio-signals of a user.

Figure 7:
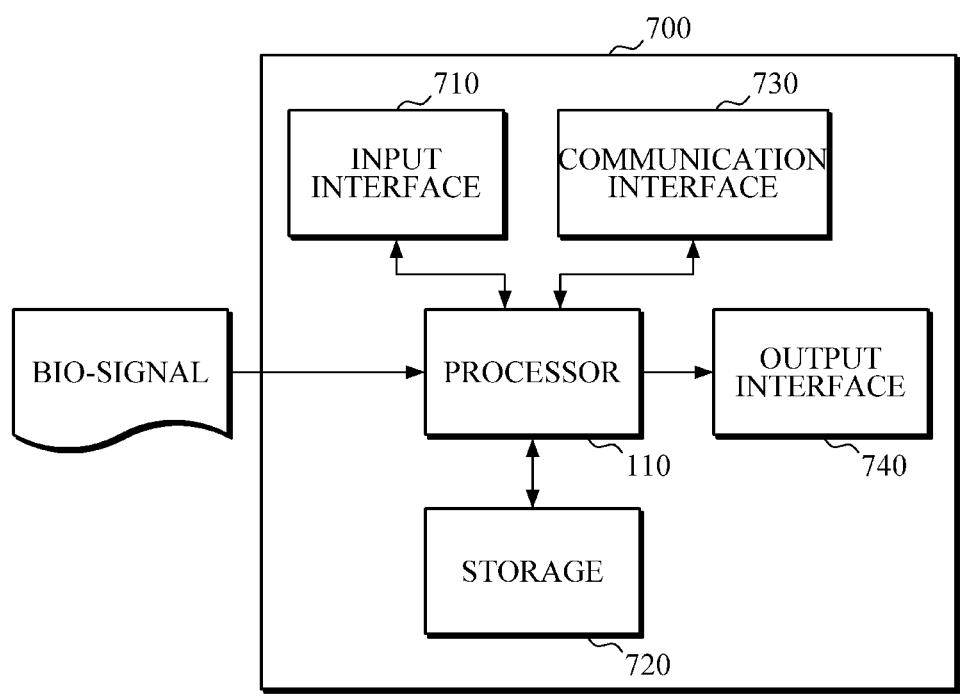
FIG. 7 is a block diagram illustrating a bio-signal quality assessment apparatus according to yet another example embodiment.

FIG. 7 is a block diagram illustrating a bio-signal quality assessment apparatus 700 according to yet another example embodiment.

Referring to FIG. 7, the bio-signal quality assessment apparatus 700 includes an input interface 710, a storage 720, a communication interface 730, an output interface 740, and a processor 110. Here, the processor 110 is the same as described above with reference to FIG. 1, and thus the detailed description thereof will be omitted.

The input interface 710 may receive various operation signals from a user. According to an example embodiment, the input interface 710 may include a key pad, a dome switch, a touch pad (resistive/capacitive) a jog wheel, a jog switch, a hardware button, and the like. When the touch pad forms a mutual layer structure with a display, it may be referred to as a touch screen.

The storage 720 may store a program or instructions for operations of the bio-signal quality assessment apparatus 700 and may store input/output data. In addition, the storage 720 may store moving average data of a bio-signal and data regarding a calculated number of bio-signal samples in each section that have values greater than the moving average.

The storage 720 may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, an optical disk, and the like. In addition, the bio-signal quality assessment apparatus 700 may operate an external storage medium, such as a web storage, which performs the storage function of the storage 720 on the Internet.

The communication interface 730 may perform communications with an external device. For example, the communication interface 730 may transmit data input from the user through the input interface 710 or bio-signal quality assessment data of the processor 110 to the external device, or may receive various data helpful for a bio-signal quality assessment from the external device.

In this case, the external device may be a medical device that uses measured skin spectrum data, a printer for outputting a result, or a display device that displays a blood vessel pattern recognition result information or skin spectrum information. In addition, the external device may be a digital TV, a desktop computer, a mobile phone, a smartphone, a tablet computer, a notebook computer, a PDA, a PMP, a navigation system, an MP3 player, a digital camera, a wearable device, or the like, but is not limited thereto.

The communication interface 730 may communicate with the external device using a Bluetooth communication, Bluetooth low energy (BLE) communication, a near-field communication (NFC), a wireless local area network (WLAN) communication, a ZigBee communication, an infrared data association (IrDA) communication, a Wi-Fi direct (WFD) communication, a ultra-wideband (UWB) communication, an Ant+ communication, a Wi-Fi communication, a radio frequency identification (RFID) communication, a 3G communication, a 4G communication, a 5G communication, and the like. However, the above description is provided for the purpose of example, and the type of communication is not limited thereto.

The output interface 740 may output a bio-signal quality assessment result and the like. According to an example embodiment, the output interface 740 may output the bio-signal quality assessment result and the like in any one or any combination of audible, visual, and tactile manners. For example, the output interface 740 may output the bio-signal quality assessment result and the like, using a voice, text, vibration, etc. To this end, the output interface 740 may include a display, a speaker, and a vibrator.

Figure 8:
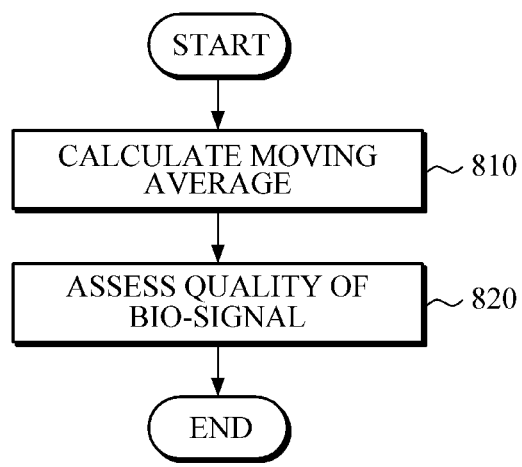
FIG. 8 is a flowchart illustrating a bio-signal quality assessment method according to an example embodiment.

FIG. 8 is a flowchart illustrating a bio-signal quality assessment method according to an example embodiment.

Referring to FIGS. 1 and 8, the bio-signal quality assessment apparatus 100 calculates a moving average of a bio-signal, as depicted in operation 810. In this case, the bio-signal may include a predetermined number of bio-signal samples, and the number of bio-signal samples included in the bio-signal may be set in advance in consideration of a periodicity of the bio-signal as a basic unit of a bio-signal quality index calculation or a bio-signal quality assessment. For example, the bio-signal quality assessment apparatus 100 may calculate the moving average of the bio-signal, using Equation 1.

The bio-signal quality assessment apparatus 100 compares the calculated moving average and the bio-signal to assess a quality of the bio-signal on the basis of a result of the comparison, as depicted in operation 820.

Hereinafter, the operation 820 of the bio-signal quality assessment method will be described in detail with reference to FIG. 9.

Figure 9:
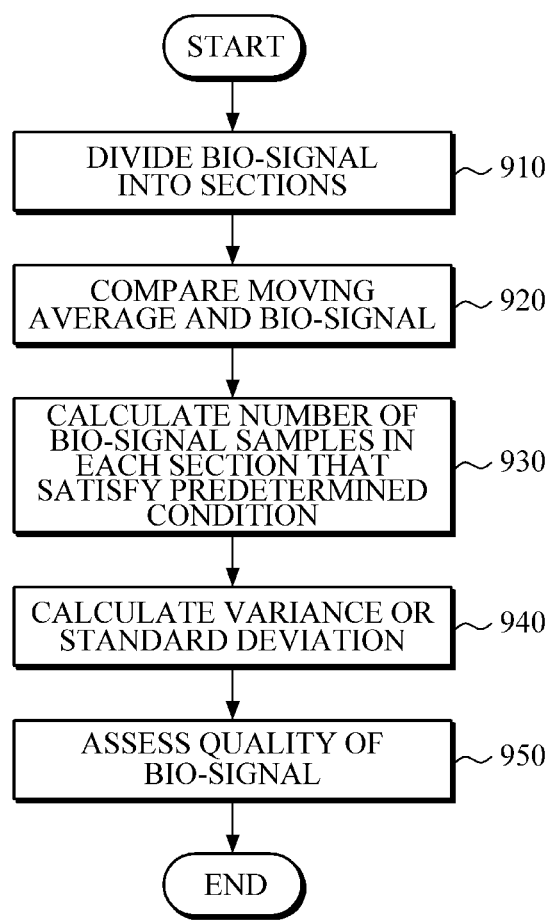
FIG. 9 is a flowchart illustrating an operation of the bio-signal quality assessment method of FIG. 8.

FIG. 9 is a flowchart illustrating the operation 820 of the bio-signal quality assessment method, according to an example embodiment.

Referring to FIGS. 1 and 9, the bio-signal quality assessment apparatus 100 divides the bio-signal into a plurality of sections, as depicted in operation 910. For example, the bio-signal quality assessment apparatus 100 may divide the bio-signal into the plurality of sections to include a predetermined number of bio-signal samples in each section. In this case, the number of bio-signal samples included in each section may be set variously according to a performance or a use of the system.

The bio-signal quality assessment apparatus 100 compares the calculated moving average and the bio-signal to determine whether this comparison satisfies a predetermined condition, as depicted in operation 920, and calculates a number of bio-signal samples in each section that satisfy the predetermined condition, as depicted in operation 930. For example, the bio-signal quality assessment apparatus 100 may calculate the number of bio-signal samples in each section that have values greater than the moving average or the number of bio-signal samples in each section that have values less than the moving average.

The bio-signal quality assessment apparatus 100 calculates a variance or a standard deviation of the calculated number of bio-signal samples in each section that satisfy the predetermined condition, as depicted in operation 940.

The bio-signal quality assessment apparatus 100 assesses the quality of the bio-signal, using the calculated variance or standard deviation as a bio-signal quality index, as depicted in operation 950. According to an example embodiment, the bio-signal quality assessment apparatus 100 may assess the quality of the bio-signal, using a criterion predefined in consideration of a relationship between the bio-signal quality index and an SNR. For example, the bio-signal quality assessment apparatus 100 may categorize the quality of the bio-signal as "high," "moderate," or "low." In detail, the bio-signal quality assessment apparatus 100 may assess the quality of the bio-signal as high when the calculated variance or standard deviation is greater than or equal to a first threshold value, assess the quality as moderate when the calculated variance or standard deviation is less than the first threshold value and greater than or equal to a second threshold value, and assess the equality as low when the calculated variance or standard deviation is less than the second threshold value. In this case, the first threshold value and the second threshold value may be set in advance in consideration of the relationship between the SNR and the bio-signal quality index. That is, the bio-signal quality assessment apparatus 100 may assess that the quality of the bio-signal is better as the calculated variance or standard deviation is larger.

Figure 10:
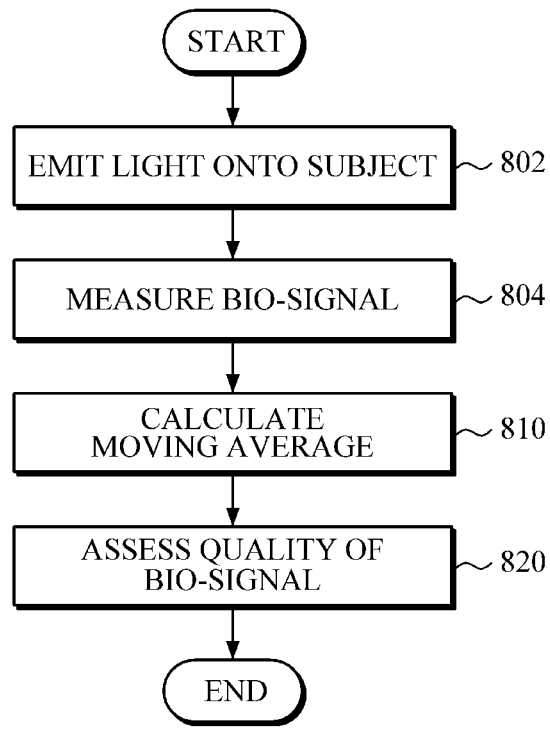
FIG. 10 is a flowchart illustrating a bio-signal quality assessment method according to another example embodiment.

FIG. 10 is a flowchart illustrating a bio-signal quality assessment method according to another example embodiment.

Referring to FIGS. 5 and 10, the bio-signal quality assessment apparatus 500 emits light onto a subject, as depicted in operation 802, and detects light reflected or scattered from the subject to measure a bio-signal, as depicted in operation 804.

The bio-signal quality assessment apparatus 500 calculates a moving average of the measured bio-signal, as depicted in operation 810. For example, the bio-signal quality assessment apparatus 500 may compute the moving average of the bio-signal, using Equation 1.

The bio-signal quality assessment apparatus 500 compares the calculated moving average and the bio-signal to assess a quality of the bio-signal, as depicted in operation 820.

Figure 11:
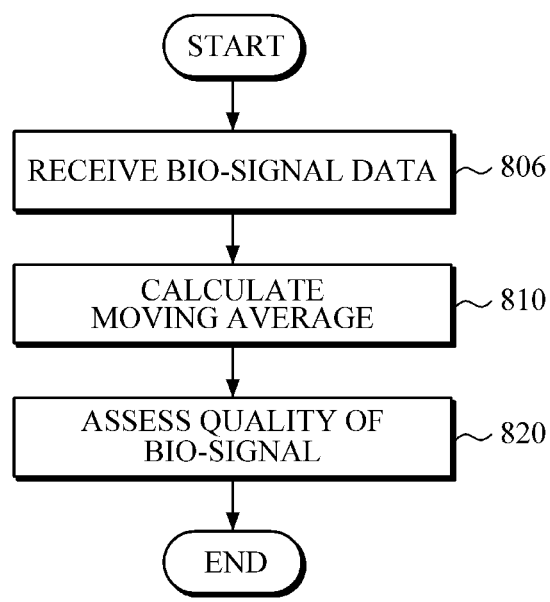
FIG. 11 is a flowchart illustrating a bio-signal quality assessment method according to still another example embodiment.

FIG. 11 is a flowchart illustrating a bio-signal quality assessment method according to still another example embodiment.

Referring to FIGS. 6 and 11, the bio-signal quality assessment apparatus 600 receives bio-signal data from a bio-signal measurement apparatus, using a communication technology, as depicted in operation 806. In this case, the communication technology may include, but is not limited to, a Bluetooth communication, BLE communication, an NFC, a WLAN communication, a ZigBee communication, an IrDA communication, a WFD communication, a UWB communication, an Ant+ communication, a Wi-Fi communication, an RFID communication, a 3G communication, a 4G communication, a 5G communication, and the like.

In response to a control signal generated according to a user input or a control signal received from the bio-signal quality assessment apparatus 600, the bio-signal measurement apparatus may measure a bio-signal by driving a light source to emit light onto a subject and receiving light reflected or scattered from the subject. The bio-signal measurement apparatus may be a wearable device that may be worn on a user's body, but this is an example embodiment, and the bio-signal measurement apparatus is not limited thereto.

The bio-signal quality assessment apparatus 600 calculates a moving average of the measured bio-signal, as depicted in operation 810. For example, the bio-signal quality assessment apparatus 600 may compute the moving average of the bio-signal, using Equation 1.

The bio-signal quality assessment apparatus 600 compares the calculated moving average and the bio-signal to assess a quality of the bio-signal, as depicted in operation 820.

Figure 12:
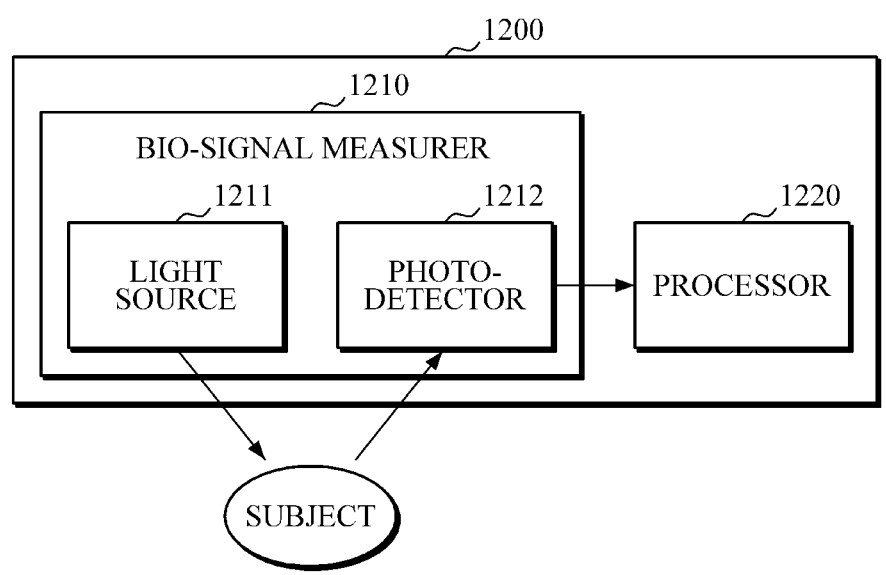
FIG. 12 is a block diagram illustrating a bio-signal measurement parameter optimization apparatus according to an example embodiment.

FIG. 12 is a block diagram illustrating a bio-signal measurement parameter optimization apparatus 1200 according to an example embodiment.

The bio-signal measurement parameter optimization apparatus 1200 may be an apparatus that assesses, in real-time, a quality of a bio-signal measured from a user through an efficient computation, and adjusts a bio-signal measurement parameter according to a result of the assessment such that a high-quality bio-signal can be obtained. The bio-signal measurement parameter optimization apparatus 1200 may be implemented in the form of a software module or fabricated in the form of a hardware chip and mounted in an electronic device. In this case, the electronic device may include a mobile phone, a smartphone, a tablet computer, a notebook computer, a PDA, a PMP, a navigation system, an MP3 player, a digital camera, a wearable device, etc., and the wearable device may include a wristwatch type, a wrist band type, a ring type, a belt type, a necklace type, an ankle band type, a thigh band type, a forearm band type and, the like. However, the electronic device is not limited to the above-described examples, and the wearable device is also not limited to the above-described examples.

Referring to FIG. 12, the bio-signal measurement parameter optimization apparatus 1200 includes a bio-signal measurer 1210 and a processor 1220.

The bio-signal measurer 1210 may measure a bio-signal of a subject. To this end, the bio-signal measurer 1210 includes a light source 1211 and a photodetector 1212.

The light source 1211 may emit light onto the subject. According to an example embodiment, the light source 1211 may include various light emitting devices, such as an LED, a laser diode, and the like.

The photodetector 1212 may detect light reflected or scattered from the subject and generate an electrical signal corresponding to a bio-signal. According to an example embodiment, the photodetector 1212 may include various light receiving elements, such as a photo diode, a photo transistor (PTr), a CCD, and the like.

The processor 1220 may compare the bio-signal and a moving average of the bio-signal, calculate a bio-signal quality index on the basis of a result of the comparison, and adjust a bio-signal measurement parameter on the basis of the calculated bio-signal quality index.

Hereinafter, the processor 1220 will be described in more detail with reference to FIG. 13.

Figure 13:
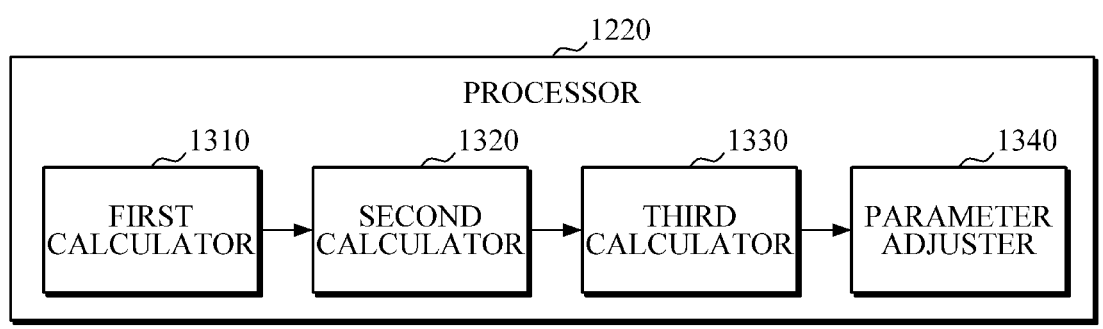
FIG. 13 is a block diagram illustrating a processor of FIG. 12.

FIG. 13 is a block diagram illustrating the processor 1220 of FIG. 12.

Referring to FIG. 13, the processor 1220 includes a first calculator 1310, a second calculator 1320, a third calculator 1330, and a parameter adjuster 1340.

The first calculator 1310 may calculate a moving average of a bio-signal. In this case, the bio-signal may include a predetermined number of bio-signal samples, and the number of bio-signal samples included in the bio-signal may be set in advance in consideration of a periodicity of the bio-signal as a basic unit of a bio-signal quality index calculation or a bio-signal quality assessment.

According to an example embodiment, the first calculator 1310 may calculate the moving average of the bio-signal, using Equation 1.

The second calculator 1320 may divide the bio-signal into a plurality of sections. According to an example embodiment, the second calculator 1320 may divide the bio-signal into the plurality of sections to include a predetermined number of bio-signal samples in each section. In this case, the number of bio-signal samples included in each section may be set variously according to a performance or a use of the system.

The second calculator 1320 may compare the calculated moving average and the bio-signal to calculate a number of bio-signal samples in each section that satisfy a predetermined condition. For example, the second calculator 1320 may calculate the number of bio-signal samples in each section that have values greater than the moving average or the number of bio-signal samples in each section that have values less than the moving average.

The third calculator 1330 may calculate a variance or a standard deviation of the number of bio-signal samples in each section that satisfy the predetermined condition.

The parameter adjuster 1340 may adjust a bio-signal measurement parameter, using the calculated variance or standard deviation as a bio-signal quality index. In this case, the bio-signal measurement parameter may include any one or any combination of an amount of light emitted by a light source, an amplification gain, and a cancellation current. The amplification gain and the cancellation current are related to an Analog Front End (AFE) of the bio-signal measurer 1210 of FIG. 12. The amplification gain is an amplification gain of an amplifier of the AFE. The cancellation current is used to change a DC level of a signal in the AFE. For example, when a range of a measurable signal is 0 to 1000 in an analog-to-digital conversion and a value of a measured signal is near 1000, there is a possibility that saturation occurs. In this case, to prevent the saturation, the DC level of the signal may be changed by subtracting the cancellation current from the value of the measured signal.

According to an example embodiment, the parameter adjuster 1340 may compare the bio-signal quality index with a third threshold value, and when the bio-signal quality index is less than the third threshold value, the parameter adjuster 1340 may adjust the bio-signal quality parameter, assuming that the measured bio-signal is of a low quality. In this case, the third threshold value may be preset to various values according to a performance or a use of the system. If the measured bio-signal is of a low quality (i.e., if the bio-signal quality index is less than the third threshold value), to obtain a high quality signal, the parameter adjuster 1340 may increase the amount of light emitted by the light source, and may appropriately adjust other parameters, e.g., the amplification gain and the cancellation current. The amplification gain and/or the cancellation current are not always increased. In addition, even if the quality of the measured bio-signal is deteriorated, to reduce power consumption, the parameter adjuster 1340 may decrease the amount of light emitted by the light source, and may appropriately adjust other parameters, e.g., the amplification gain and the cancellation current.

The bio-signal measurement parameter optimization apparatus 1200 may optimize the bio-signal measurement parameter by repeatedly performing bio-signal measurement, bio-signal quality index calculation, and parameter adjustment, so that a high-quality bio-signal can be measured.

In addition, the bio-signal measurement parameter optimization apparatus 1200 may measure a bio-signal a predetermined number of times and determine whether to adjust the parameter by taking a bio-signal quality index of each bio-signal into consideration in a comprehensive manner. In this case, the number of times of bio-signal measurement may be preset to various values according to the performance or use of the system. For example, when the number of times of bio-signal measurement is set to 3, the bio-signal measurer 1210 may measure a bio-signal three times, and the processor 1220 may compare a calculated bio-signal quality index of each bio-signal with the third threshold value. When an average of the calculated bio-signal quality indices is less than or equal to a fourth threshold value, the processor 1220 may adjust the bio-signal measurement parameter even when each of the calculated bio-signal quality indices is greater than the third threshold value. In this case, the fourth threshold value may be preset to various values according to the performance and use of the system.

Figure 14:
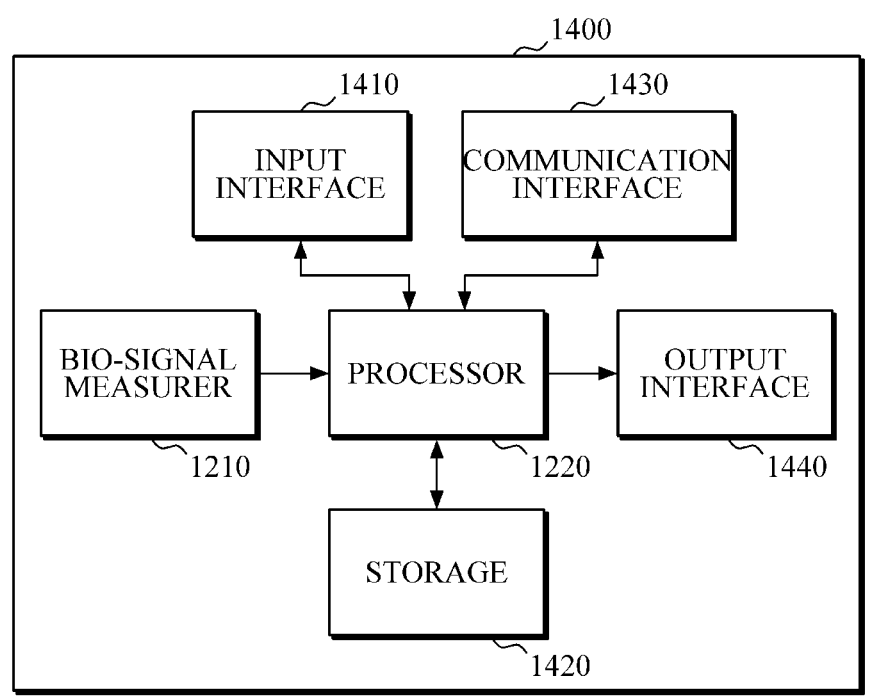
FIG. 14 is a block diagram illustrating a bio-signal measurement parameter adjustment apparatus according to another example embodiment.

FIG. 14 is a block diagram illustrating a bio-signal measurement parameter adjustment apparatus 1400 according to another example embodiment.

Referring to FIG. 14, the bio-signal measurement parameter adjustment apparatus 1400 includes an input interface 1410, a storage 1420, a communication interface 1430, an output interface 1440, a bio-signal measurer 1210, and a processor 1220. The bio-signal measurer 1210 and the processor 1220 are the same as described above with reference to FIG. 13, and thus the detailed description thereof will be omitted.

The input interface 1410 may receive various operation signals from a user. According to an example embodiment, the input interface 1410 may include a key pad, a dome switch, a touch pad (resistive/capacitive) a jog wheel, a jog switch, a hardware button, and the like. When the touch pad forms a mutual layer structure with a display, it may be referred to as a touch screen.

The storage 1420 may store a program or instructions for operations of the bio-signal measurement parameter optimization apparatus 1400 and may store input/output data. The storage 1420 may include a flash memory, a hard disk, a micro type multimedia card, and a card type memory (e.g., SD or XD memory), a RAM, an SRAM, a ROM, an EEPROM, a PROM, a magnetic memory, a magnetic disk, an optical disk, and the like. In addition, the bio-signal measurement parameter optimization apparatus 1400 may operate an external storage medium, such as a web storage, which performs the storage function of the storage 1420 on the Internet.

The communication interface 1430 may communicate with an external device. For example, the communication interface 1430 may transmit data input from the user through the input interface 1410 or bio-signal quality assessment data of the processor 1220 to the external device, or may receive various data helpful for a bio-signal quality assessment from the external device.

The output interface 1440 may output a bio-signal quality assessment result, a bio-signal measurement parameter adjustment result, and the like. According to an example embodiment, the output interface 1440 may output the bio-signal quality assessment result, the bio-signal measurement parameter adjustment result, and the like in any one or any combination of audible, visual, and tactile manners. For example, the output interface 1440 may output the bio-signal quality assessment result, the bio-signal measurement parameter adjustment result, and the like, using a voice, text, vibration, etc. To this end, the output interface 1440 may include a display, a speaker, and a vibrator.

Figure 15:
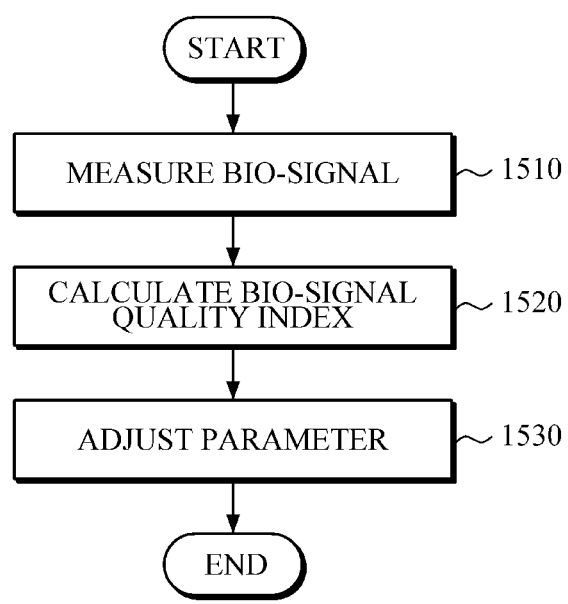
FIG. 15 is a flowchart illustrating a bio-signal measurement parameter optimization method according to an example embodiment.

FIG. 15 is a flowchart illustrating a bio-signal measurement parameter optimization method according to an example embodiment.

Referring to FIGS. 12 and 15, the bio-signal measurement parameter optimization apparatus 1200 measures a bio-signal of a subject, as depicted in operation 1510. For example, the bio-signal measurement parameter optimization apparatus 1200 may emit light onto the subject and measure the bio-signal by detecting light reflected or scattered from the subject.

The bio-signal measurement parameter optimization apparatus 1200 compares the bio-signal and a moving average of the bio-signal to calculate a bio-signal quality index on the basis of a result of the comparison, as depicted in operation 1520.

The bio-signal measurement parameter optimization apparatus 1200 adjusts a bio-signal measurement parameter on the basis of the calculated bio-signal quality index, as depicted in operation 1530. In this case, the bio-signal measurement parameter may include any one or any combination of an amount of light emitted by a light source, an amplification gain, and a cancellation current. According to an example embodiment, the bio-signal measurement parameter optimization apparatus 1200 may compare the bio-signal quality index with a third threshold value, and when the bio-signal quality index is less than the third threshold value, the bio-signal measurement parameter optimization apparatus 1200 may adjust the bio-signal quality parameter, assuming that the measured bio-signal is of a low quality. In this case, the third threshold value may be preset to various values according to a performance or a use of the system.

Figure 16:
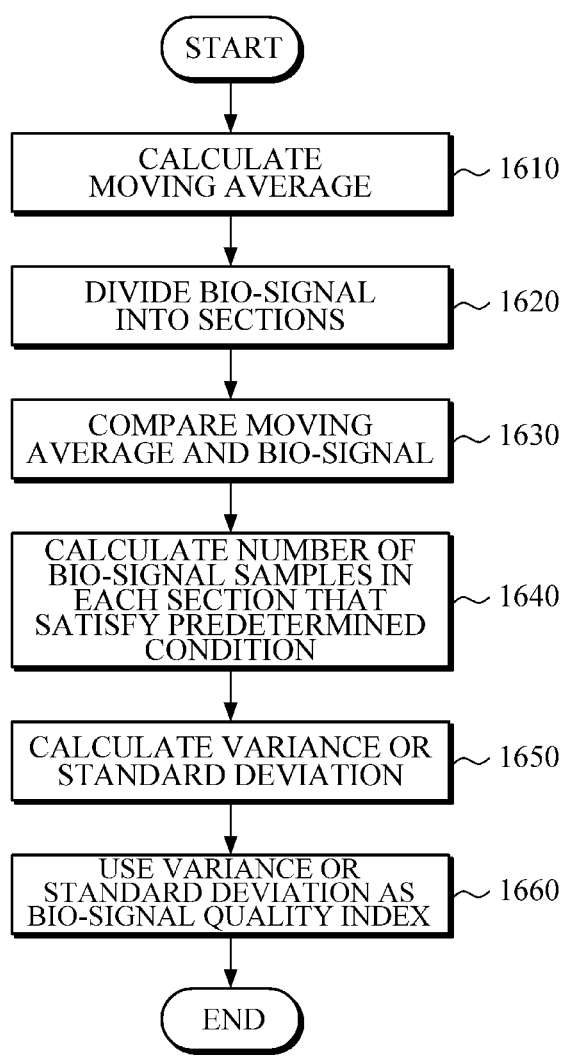
FIG. 16 is a flowchart illustrating an operation of the bio-signal measurement parameter optimization method of FIG. 15.

FIG. 16 is a flowchart illustrating the operation 1520 of bio-signal measurement parameter optimization method of FIG. 15.

Referring to FIGS. 12 and 16, the bio-signal measurement parameter optimization apparatus 1200 calculates the moving average of the bio-signal, as depicted in operation 1610. For example, the bio-signal measurement parameter optimization apparatus 1200 may calculate the moving average (e.g., an exponentially weighted moving average) of the bio-signal, using Equation 1.

The bio-signal measurement parameter optimization apparatus 1200 divides the bio-signal into a plurality of sections, as depicted in 1620. For example, the bio-signal measurement parameter optimization apparatus 1200 may divide the bio-signal into the plurality of sections to include a predetermined number of bio-signal samples in each section. In this case, the number of bio-signal samples included in each section may be set variously according to the performance or use of the system.

The bio-signal measurement parameter optimization apparatus 1200 compares the calculated moving average and the bio-signal to determine whether this comparison satisfies a predetermined condition, as depicted in operation 1630, and calculates a number of bio-signal samples in each section that satisfy the predetermined condition, as depicted in operation 1640. For example, the bio-signal measurement parameter optimization apparatus 1200 may calculate the number of bio-signal samples in each section that have values greater than the moving average or the number of bio-signal samples in each section that have values less than the moving average.

The bio-signal measurement parameter optimization apparatus 1200 calculates a variance or a standard deviation of the calculated number of bio-signal samples in each section that satisfy the predetermined condition, as depicted in operation 1650.

The bio-signal measurement parameter optimization apparatus 1200 uses the calculated variance or standard deviation as the bio-signal quality index, as depicted in operation 1660.

Figure 17:
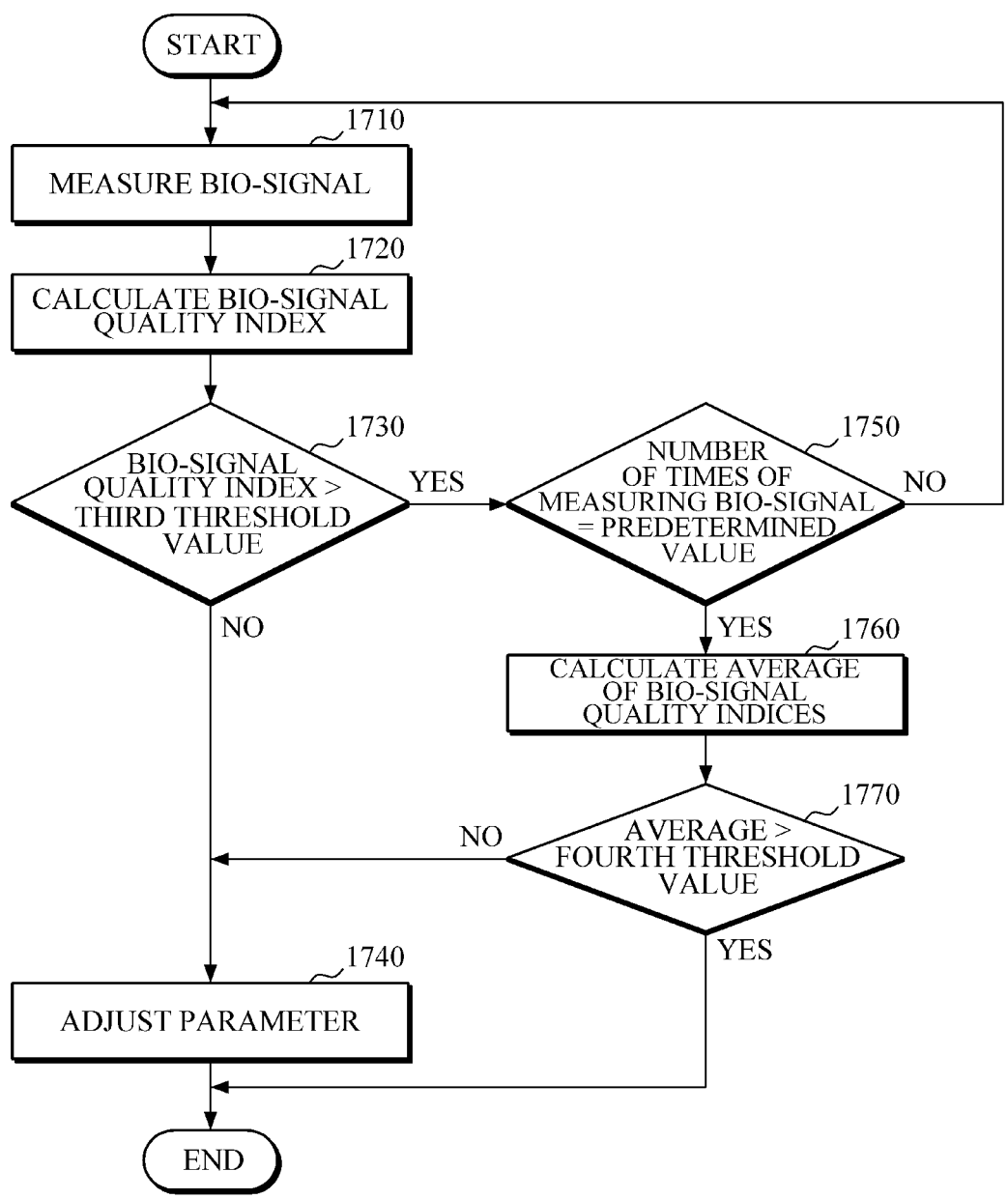
FIG. 17 is a flowchart illustrating a bio-signal measurement parameter optimization method according to still another example embodiment.

FIG. 17 is a flowchart illustrating a bio-signal measurement parameter optimization method according to another example embodiment.

Referring to FIGS. 12 and 17, the bio-signal measurement parameter optimization apparatus 1200 measures a bio-signal of a subject, as depicted in operation 1710. For example, the bio-signal measurement parameter optimization apparatus 1200 may emit light onto the subject and measure the bio-signal by detecting light reflected or scattered from the subject.

The bio-signal measurement parameter optimization apparatus 1200 compares the bio-signal and a moving average of the bio-signal to calculate a bio-signal quality index on the basis of a result of the comparison, as depicted in operation 1720.

The bio-signal measurement parameter optimization apparatus 1200 compares the calculated bio-signal quality index with a third threshold value, as depicted in operation 1730, and when the bio-signal quality index is less than or equal to the third threshold value, the bio-signal measurement parameter optimization apparatus 1200 determines that the measured bio-signal is of a low quality, and adjusts a bio-signal measurement parameter, as depicted in operation 1740.

When the calculated bio-signal quality index is greater than the third threshold value, the bio-signal measurement parameter optimization apparatus 1200 determines whether a number of times of measuring the bio-signal is equal to a predetermined value, as depicted in operation 1750, and when the number of times of measuring the bio-signal is not equal to the predetermined value, the operation flow returns to operation 1710 and the bio-signal is measured.

When the number of times of measuring the bio-signal is equal to the predetermined value, the bio-signal measurement parameter optimization apparatus 1200 calculates an average of bio-signal quality indices of bio-signals, as depicted in 1760, compares the calculated average with a fourth threshold value, as depicted in operation 1770, and when the calculated average is less than or equal to the fourth threshold value, adjusts the bio-signal measurement parameter, as depicted in operation 1740. When the calculated average is greater than the fourth threshold value, the bio-signal measurement parameter optimization method ends.

The current example embodiments can be implemented as computer readable codes in a computer readable record medium. Codes and code segments constituting the computer program can be inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A bio-signal quality assessment apparatus comprising:
a processor configured to:
   determine a moving average of a measured bio-signal;
   divide the measured bio-signal into sections;
   compare each of a plurality of values of a plurality of bio-signal samples of the measured bio-signal with the determined moving average;
   determine a number of bio-signal samples having a value greater than the determined moving average in each of the sections as a result of the comparison;
   determine a variance or a standard deviation of the determined number of bio-signal samples in each of the sections;
   determine a quality of the measured bio-signal as being a first quality when the variance or the standard deviation of the determined number of bio-signal samples is greater than or equal to a threshold value;
   determine the quality of the measured bio-signal as being a second quality when the variance or the standard deviation of the determined number of bio-signal samples is less than the threshold value; and
   adjust, based on the quality of the determined bio-signal, any one or any combination of an amount of an emitted light, an amplification gain of a measuring of the bio-signal, and a cancellation current of a measuring of the bio-signal;
   wherein a signal-to-noise ratio (SNR) of the measured bio-signal is positively correlated with the variance or the standard deviation of the determined number of bio-signal samples.

2. The bio-signal quality assessment apparatus of claim 1, wherein the bio-signal is a photoplethysmography signal.

3. The bio-signal quality assessment apparatus of claim 1, wherein the moving average is an exponentially weighted moving average.

4. The bio-signal quality assessment apparatus of claim 1, wherein the processor is further configured to assess that the quality of the measured bio-signal is better as the determined variance or the determined standard deviation is larger than the threshold value.

5. The bio-signal quality assessment apparatus of claim 1, further comprising a bio-signal measurer configured to measure the bio-signal.

6. The bio-signal quality assessment apparatus of claim 5, wherein the bio-signal measurer comprises:
   a light source configured to emit the light onto a subject; and
   a photodetector configured to measure the bio-signal by detecting light that is reflected or scattered from the subject.

7. The bio-signal quality assessment apparatus of claim 1, further comprising a data receiver configured to receive data of the bio-signal from an external device.

8. A bio-signal quality assessment method comprising:
determining a moving average of a measured bio-signal;
dividing the measured bio-signal into sections;
comparing each of a plurality of values of a plurality of bio-signal samples of the measured bio-signal with the determined moving average;
determining a number of bio-signal samples having a value greater than the determined moving average in each of the sections as a result of the comparison;
determining a variance or a standard deviation of the determined number of bio-signal samples in each of the sections;
determining a quality of the measured bio-signal as being a first quality when the variance or the standard deviation of the determined number of bio-signal samples is greater than or equal to a threshold value;
determining the quality of the measured bio-signal as being a second quality when the variance or the standard deviation of the determined number of bio-signal samples is less than a threshold value; and
adjusting, based on the quality of the determined bio-signal, any one or any combination of an amount of an emitted light, an amplification gain of a measuring of the bio-signal, and a cancellation current of a measuring of the bio-signal,
wherein a signal-to-noise ratio (SNR) of the measured bio-signal is positively correlated with the variance or the standard deviation of the determined number of bio-signal samples.

9. The bio-signal quality assessment method of claim 8, wherein the assessing of the quality of measured the bio-signal further comprises assessing that the quality of the measured bio-signal is better as the determined variance or the determined standard deviation is larger than the threshold value.

10. The bio-signal quality assessment method of claim 8, wherein the bio-signal is a photoplethysmography signal.

11. The bio-signal quality assessment method of claim 8, wherein the moving average is an exponentially weighted moving average.

12. The bio-signal quality assessment method of claim 8, further comprising measuring the bio-signal.

13. The bio-signal quality assessment method of claim 12, further comprising emitting the light onto a subject,
wherein the measuring of the bio-signal comprises measuring the bio-signal by detecting light that is reflected or scattered from the subject.

14. The bio-signal quality assessment method of claim 8, further comprising receiving data of the bio-signal from an external device.

15. A bio-signal measurement parameter optimization apparatus comprising:
a bio-signal measurer configured to:
emit light onto a subject; and
measure a bio-signal by detecting light that is reflected or scattered from the subject; and
a processor configured to:
determine a moving average of the measured bio-signal;
divide the measured bio-signal into sections;
compare each of a plurality of values of a plurality of bio-signal samples of the measured bio-signal with the determined moving average;
determine a number of bio-signal samples having a value greater than the determined moving average in each of the sections as a result of the comparison;
determine a variance or a standard deviation of the determined number of bio-signal samples in each of the sections;
determine a quality of the measured bio-signal as being a first quality when the variance or the standard deviation of the determined number of bio-signal samples is greater than or equal to a threshold value; and
determine the quality of the measured bio-signal as being a second quality when the variance or the standard deviation of the determined number of bio-signal samples is less than the threshold value, wherein a signal-to-noise ratio (SNR) of the measured bio-signal is positively correlated with the variance or the standard deviation of the determined number of bio-signal samples, and
adjust, based on the determined quality of the measured bio-signal, any one or any combination of an amount of the emitted light, an amplification gain of the bio-signal measurer, and a cancellation current of the bio-signal measurer.

16. The bio-signal measurement parameter optimization apparatus of claim 15, wherein the bio-signal is a photoplethysmography signal.

17. The bio-signal measurement parameter optimization apparatus of claim 15, wherein the moving average is an exponentially weighted moving average.

18. The bio-signal measurement parameter optimization apparatus of claim 15, wherein the processor is further configured to, in response to the determined quality of the measured bio-signal being the second quality, adjust any one or any combination of the amount of the emitted light, the amplification gain, and the cancellation current.

19. The bio-signal measurement parameter optimization apparatus of claim 18, wherein the processor is further configured to:
in response to the determined quality of the measured bio-signal being greater than the threshold value, determine whether a number of times of measuring the bio-signal corresponds to a predetermined value;
in response to the number of times of measuring the bio-signal being determined to not correspond to the predetermined value, measure another bio-signal;
in response to the number of times of measuring the bio-signal being determined to correspond to the predetermined value, determine bio-signal quality indices of a plurality of bio-signals that are measured, and determine an average of the determined bio-quality indices; and
in response to the determined average of the bio-signal quality indices being less than or equal to a threshold value, adjust any one or any combination of the amount of the emitted light, the amplification gain, and the cancellation current.

20. A bio-signal measurement parameter optimization method comprising:
emitting light onto a subject;
measuring a bio-signal by detecting light that is reflected or scattered from the subject;
determining a moving average of the measured bio-signal;
dividing the measured bio-signal into sections;
comparing each of a plurality of values of a plurality of bio-signal samples of the measured bio-signal with the determined moving average;

determining a number of bio-signal samples having a value greater than the determined moving average in each of the sections as a result of the comparison;

determining a variance or a standard deviation of the determined number of bio-signal samples in each of the sections;

determining a quality of the measured bio-signal as being a first quality when the variance or the standard deviation of the determined number of bio-signal samples is greater than or equal to a threshold value;

determining the quality of the measured bio-signal as being a second quality when the variance or the standard deviation of the determined number of bio-signal samples is less than the threshold value, wherein a signal-to-noise ratio (SNR) of the measured bio-signal is positively correlated with the variance or the standard deviation of the determined number of bio-signal samples; and adjusting, based on the quality of the determined bio-signal, any one or any combination of an amount of the emitted light, an amplification gain of the measuring of the bio-signal, and a cancellation current of the measuring of the bio-signal.

21. The bio-signal measurement parameter optimization method of claim 20, wherein the adjusting comprises, in response to the determined quality of the measured bio-signal being the second quality, adjust any one or any combination of the amount of the emitted light, the amplification gain, and the cancellation current.

* * * * *